United States Patent
Herzberg et al.

[11] Patent Number: 6,099,489
[45] Date of Patent: Aug. 8, 2000

[54] MEDICAL BANDAGE

[75] Inventors: Thorsten Herzberg; Thorsten Stradt, both of Hamburg; Andreas Albrod, Seevetal; Harald Votsch; Oliver Reichert, both of Hamburg; Arthur-Hugh Andrews, Kölln-Reisiek; Brigitte Rosenbaum, Hamburg, all of Germany

[73] Assignee: Beiersdorf AG, Hamburg, Germany

[21] Appl. No.: 09/173,280

[22] Filed: Oct. 15, 1998

[30] Foreign Application Priority Data

Oct. 16, 1997 [DE] Germany .................. 197 45 705

[51] Int. Cl.⁷ .................. A61F 5/00; A61F 13/00; A61F 5/37; A61F 5/02
[52] U.S. Cl. .................. 602/4; 602/20; 602/21; 602/62; 128/876; 128/878; 2/45
[58] Field of Search .................. 602/4, 20, 26, 602/61, 62, 64, 65, 5, 60; 2/24, 455, 44, 45; 128/877, 878, 879, 880, 881, 882

[56] References Cited

U.S. PATENT DOCUMENTS

| 1,490,381 | 4/1924 | Gobar .................. 602/4 |
| 3,404,650 | 10/1968 | Gutman et al. .................. 602/4 |
| 4,437,459 | 3/1984 | Slavetskas .................. 602/4 |
| 5,413,552 | 5/1995 | Iwuala .................. 602/4 |
| 5,830,165 | 11/1998 | Rowe et al. .................. 602/4 |

FOREIGN PATENT DOCUMENTS 198782 10/1986 European Pat. Off. .................. 602/4

*Primary Examiner*—Kim M. Lee
*Attorney, Agent, or Firm*—Norris, McLaughlin & Marcus, P.A.

[57] ABSTRACT

Medical arm bandage which surrounds and guides the forearm and the upper arm and shoulder.

8 Claims, 3 Drawing Sheets

MEDICAL BANDAGE

BACKGROUND OF THE INVENTION

The invention describes a medical arm bandage to surround and guide the forearm and the upper arm and shoulder.

Depending on their design and their field of indication, orthopaedic bandages exert a fixing, guiding, supporting and/or assisting function on the limbs of the human body.

These medical bandages have to have a three-dimensional shape to correspond to the anatomical conditions, so as to be able to act on the human body from the outside with a form fit and friction fit.

Medical bandages of this type are produced by cutting out blanks from sheet-like material, for example from neoprene, knits or woven fabrics. The anatomically adapted shape is achieved by the shape of the blanks or darts, for example using gusseting, and the subsequent joining together of the blanks, as is also customary in clothing.

The joining together can be done by sewing, gluing and other usual methods.

Another possible way of producing the medical bandages is shaped knitting using flat-knitting machines or circular-knitting machines. However, this method is limited in terms of the possibility of shaping and the choice of materials. In particular, only two-dimensional shaping is possible. The third dimension is only obtainable by subsequent sewing together.

Bandages in which foam rubber is deformed by compression molding to give different thicknesses are also known. The intention thereby is for the elastic properties of the material to be changed locally due to the differing density of the foam after the deformation. A bandage of this type is, for example, described in WO 95/32690.

It is furthermore known to shape thermoplastic plates in suitable anatomical form so as to give orthopaedic ortheses and prostheses. These materials, e.g. polyethylene (HDPE), polypropylene or a polypropylene copolymer, have a thermoplastic deformation range of approximately 170° C. to 250° C. and are substantially rigid after cooling, so that they are not used for medical bandages.

DE P 43 14 785 discloses a bandage system, in particular for acromioclavicular dislocations and lateral clavicular fractures. The bandage system is composed of a tubular part which accommodates the forearm and the upper arm and consists of a radially elastic woven material which is, however, essentially non-extendable in the longitudinal direction, a supporting band, a holding band, fastening means which are provided on the abovementioned bands in order to form holding loops, and a tensile strap. A bandage of this type is indeed suitable to alleviate the specified indications, but it is very complex to produce. Furthermore, the tubular design often makes it difficult for the patient to put the bandage on without pain.

The generally known bandages for this sphere of indication have a tightly closed design which inevitably leads to it only being possible for the bandages to be put on without pain with an additional person assisting. These bandages very frequently also result in unpleasant sweating with heat accumulating because of the generally closed design.

The more simply designed bandages, which generally only comprise two straps, do not have the sweating problem but their design means that they are generally questionable and thus unsatisfactory with regard to their treatment reliability and function.

The object of the invention was therefore to provide a bandage which has an open design and a high degree of treatment reliability, and which can be put on without pain without a third party assisting.

SUMMARY OF THE INVENTION

This object is achieved by means of a bandage (100) adapted for use on the shoulder and upper-arm region of a user, comprising an upper-arm part (1) and a forearm Dart (2), the upper-arm part (1) being of U-shaped design, and having a mouth (11), which lies in a region of the upper-arm part (1) in which a first limb (12) and a second limb (13) converge, is adapted to rest upon the shoulder during use, the first limb (12) is adapted to extend from the shoulder at the front of the user approximately as far as the elbow joint, and the second limb (13) adapted to extend at the rear approximately as far as the elbow joint, and the forearm part (2) being formed from three sections (21), (22), (23), a central first section (21) which, when the forearm is bent in front at an angle of approximately 90°, is adapted to lie in the ulnar region of the forearm during use, a second section (22) which is connected to the second limb (13) of the upper-arm part (1) adapted to extend at the rear over the elbow joint and merges into the first section (21) during use, a third section (23) which is connected to the first limb (12) of the upper-arm part (1) is adapted to extend at the front over the elbow joint and merges into the first section (21) during use, the ends of the second section (22) and the third section (23) being connected to one another, a supporting strap (3) being attached to the upper-arm part (1) and a holding strap (4) being attached to the forearm part (2).

DETAILED DESCRIPTION

Accordingly, the bandage for the shoulder and upper-arm region comprises an upper-arm part and a forearm part. The upper-arm part is of U-shaped design, the mouth, which indicates that region of the upper-arm part in which the first limb and the second limb converge, resting upon the shoulder of the patient, the first limb extending at the front approximately as far as the elbow joint, and the second limb extending at the rear approximately as far as the elbow joint.

The forearm part is formed from three sections, a first section which, with the forearm bent in front at an angle of approximately 90°, lies in the ulnar forearm region, a second section which is connected to the second limb of the upper-arm part and which runs at the rear over the elbow joint and merges into the first section, a third section which is connected to the first limb of the upper-arm part and which runs at the front over the elbow joint and merges into the first section, the ends of the second section and the third section being connected to one another. Furthermore, a supporting strap is attached to the upper-arm part and a holding strap is attached to the forearm part to fix the bandage according to the invention on the body. When the bandage is not sewn up, the second section and the third section of the forearm part enclose an angle of 20° to 150°, preferably 60° to 120°.

The upper-arm part and the forearm part can be connected to one another by means of a touch-and-close connection, by means of press-studs or seams. In particular, there is an adjustable connection for adaptation to the individual limb lengths and thus to improve the efficiency of fit.

In a preferred embodiment, elastic sections are present in the upper-arm part, at the ends of the limbs.

These elastic sections in the distal upper-arm part ensure ideal, individual adaptation to the anatomical shaping in the region of the shoulder and upper arm and of the elbow. As a result, the shoulder portion and, in particular, the head of the upper arm are guided securely.

It has proven advantageous if the components of the bandage consist of a textile-lined foam or nonwoven or of a shaped foam or nonwoven.

In a further advantageous embodiment, an appropriately shaped reinforcement is present in the upper-arm part, centrally in the mouth region. This reinforcement can likewise be of U-shaped design. The reinforcement is preferably made of plastic and has the shape of a bar or a rail.

In a further advantageous embodiment, the forearm part has a hand guide or hand-fixing means. The hand guide can optionally be adapted individually, in accordance with the treatment and the indication, so as to ensure an optimum fit.

The hand guide guides the hand and thus prevents excessive ulnar flexion; it furthermore counteracts overstretching of the tendons and of the ligament apparatus, which are generally very sensitive in the volar region.

The hand guide may comprise two restraints which adjoin the first section of the forearm part, specifically in the distal forearm region. The two restraints enclose an angle of 10° to 160°, in particular 90°. The restraints can be connected to one another by means of touch-and-close fasteners at the distal end of the restraints, and the hand is thus securely fixed.

It has also proven advantageous in the case of the forearm part if reinforcements which are in the form of a bar or a rail and are produced from plastic are incorporated into the first section.

The upper-arm part can be fixed ventrally with respect to the forearm in the region of the wrist by means of a supporting strap which runs from the shoulder to the anterial thorax region, it being possible for the supporting strap to contain a partial cushion in the transition region from the cervical vertebral column to the shoulder girdle.

The supporting strap ensures that the upper-arm part is securely positioned and relieves the weight of the forearm, which has a positive effect on the shoulder joint. The shoulder joint is usually subject to a constant force action because of the weight of the forearm. This tensile force has a disadvantageous effect on the tendon and ligament apparatus of the shoulder joint.

The holding strap of the forearm part advantageously runs from the hand region dorsally in the lumbar region to the distal upper arm and surrounds the latter laterally from the rear to the front. The holding strap ensures that the forearm is securely fixed against the ventral area. The holding of the distal upper arm causes the movement in terms of flexion or extension and also of anti-torsion of the shoulder joint to be guided in a controlled manner.

The straps may be fixed by touch-and-close fasteners or by press-studs, for example.

The straps preferably consist of a laminated foam or a laminated nonwoven.

Finally, it has proven advantageous if the straps have a good cushioning effect and under a load of approximately 50 N have a preferred longitudinal extension of less than 35%, particularly preferably a longitudinal extension of less than 10%.

The bandage according to the invention is used, in particular, as a special post-traumatic and post-operative bandage for injuries in the shoulder and upper-arm region, for example distortions, rotator cuff injuries and other injuries, operative interventions and chronic afflictions which require the shoulder to be in a rest position.

A special bandage of this type has to have the properties according to the invention so as to be able to act in the manner which is appropriate for the indication:

an explicit fitting shape in order to ensure that the shoulder and upper arm are securely and stably fixed;

a well-surrounded shoulder joint with a corresponding fixing transition to the thoracic region.

Depending on the field of indication, a fixing means for the forearm with an integrated hand guide is also required in order to have a high degree of certainty regarding the success of the treatment. As is similarly the case with conventional plaster treatment, in the case of an affected joint one or two joints are always spanned in order to ensure effective treatment.

These criteria are fulfilled by the refinement, according to the invention, of the upper-arm part and the forearm part, which corresponds to the anatomical conditions of the arm and the shoulder.

The open design makes it possible, moreover, for the bandage according to the invention to be put on in a simple manner without pain. This is a particular advantage, especially since the patient can put on the bandage himself. Moreover, sweating, which is a very unpleasant sensation for the patient, is suppressed to a very great extent.

In the following, a particularly advantageous design of the bandage according to the invention is to be described by means of several figures without the invention being unnecessarily restricted thereto.

In the drawings:

BRIEF DESCRIPTION OF THE DRAWINGS

FIG. 1 shows the upper-arm part 1. The upper-arm part 1 is shaped in a U-shape in such a manner that it is extremely well adapted to the anatomical conditions of the upper arm and the shoulder of the patient. The upper-arm part 1 comprises two limbs 12, 13, which converge in the mouth 11. When the bandage 100. (FIG. 5) is put on, the mouth 11 is situated on the patient's shoulder. A reinforcement 16 which is designed in the shape of a bar and is made of plastic is incorporated into the mouth 11. The supporting strap 3 is sewn centrally onto the mouth 11, to be precise opposite the limbs 12, 13.

Figure 1:
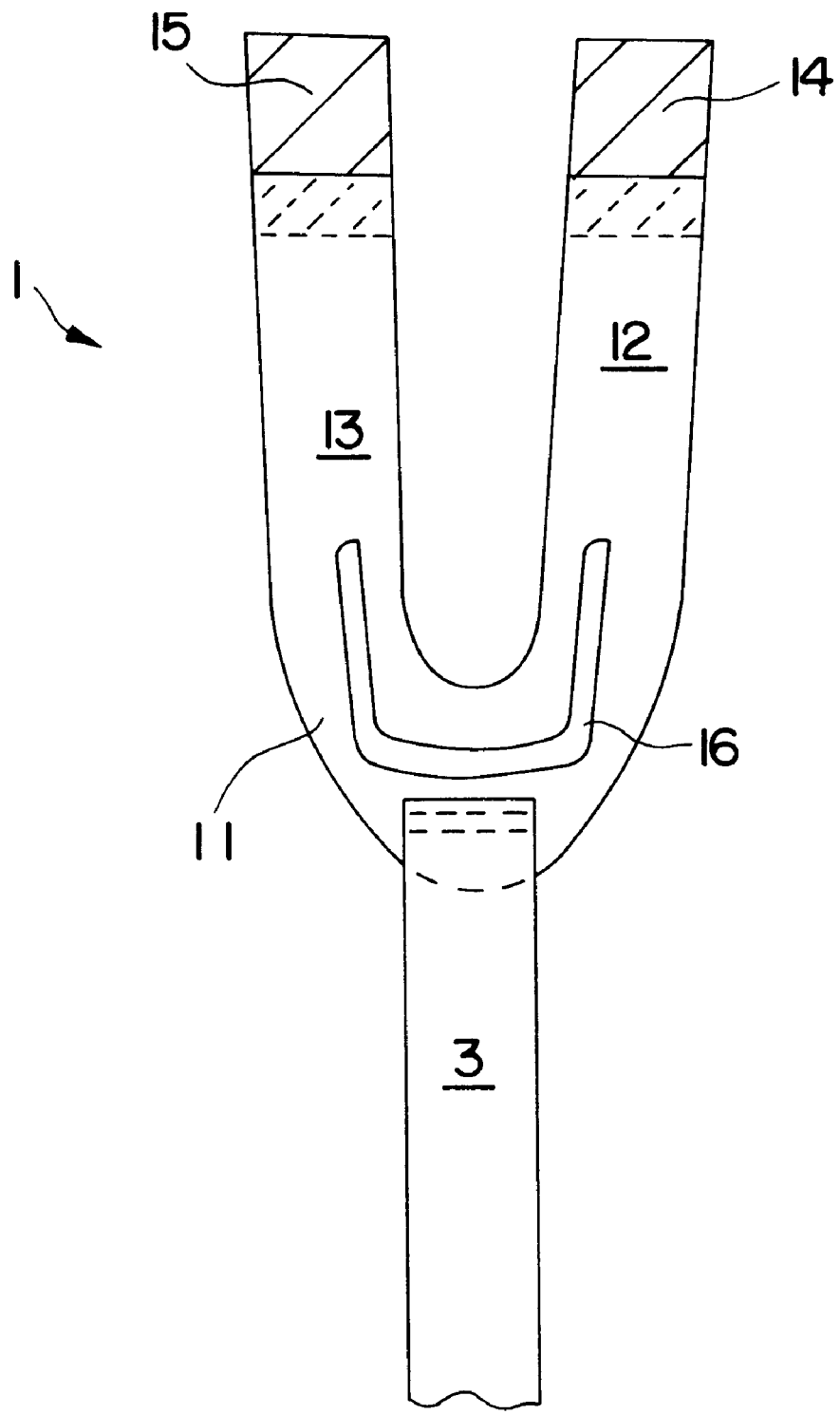
FIG. 1 shows the upper-arm part.

Two elastic sections 14, 15 are situated at the ends of the essentially rectangularly shaped limbs 12, 13, which sections, because of their flexibility, ensure an optimum fit of the bandage 100. The elastic sections 14, 15 are sewn to the second section 22 and third section 23, respectively, of the forearm part 2 (FIG. 2).

Figure 2:
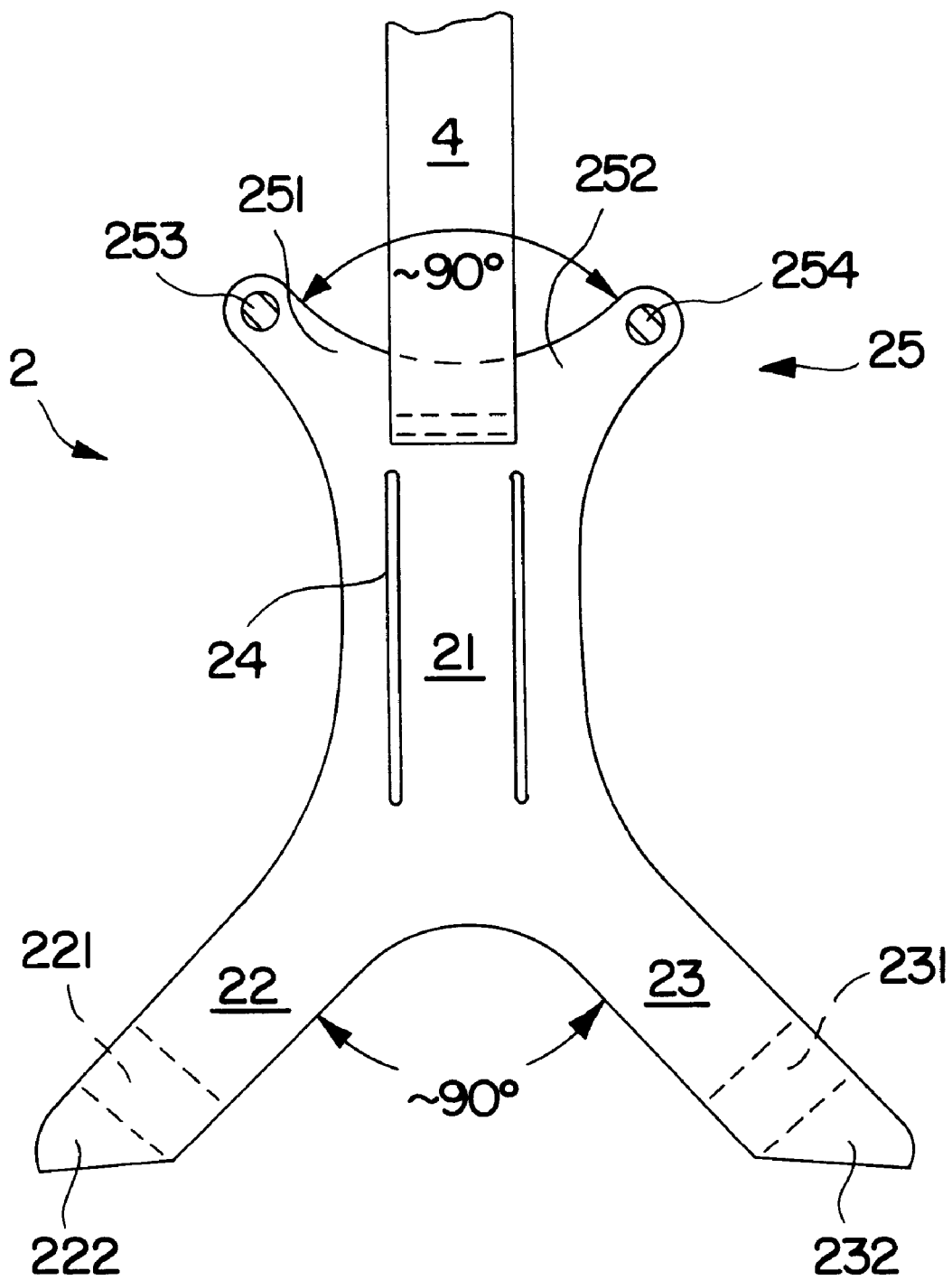
FIG. 2 shows the forearm part with the sewing seams opened up.

FIG. 2 shows the forearm part 2, the seams which are present having been opened up. The forearm part 2 has a total of three sections 21, 22, 23. The central, first section 21 lies in the ulnar forearm region. The first section 21 is adjoined by the second section 22 and by the third section 23, which enclose an angle of approximately 90°. In the finished bandage 100, the ends 222, 232 of the sections 22, 23 are sewn together. This produces, a shell-shaped bulge which is extremely well adapted to the anatomical conditions of the elbow joint and in which the elbow can be accommodated.

The elastic section 14 of the first limb 12 of the upper-arm part is sewn on in the region 221, and the elastic section 15 is sewn on in the region 231. The first section 21 furthermore bears rail-shaped reinforcements 24, which are likewise manufactured from plastic. In the advantageous embodiment of the bandage 100 which is represented here, there is integrally molded onto the forearm part 2 a hand-fixing means 25 which is composed of two restraints 251, 252 which enclose an angle of 90°. At the ends of the restraints 251, 252 are situated two touch-and-close fasteners 253, 254 which are connected to one another in such a manner that the hand-fixing means 25 surrounds the patient's hand. The holding strap 4 is fastened centrally to the hand-fixing means 25.

Figure 3:
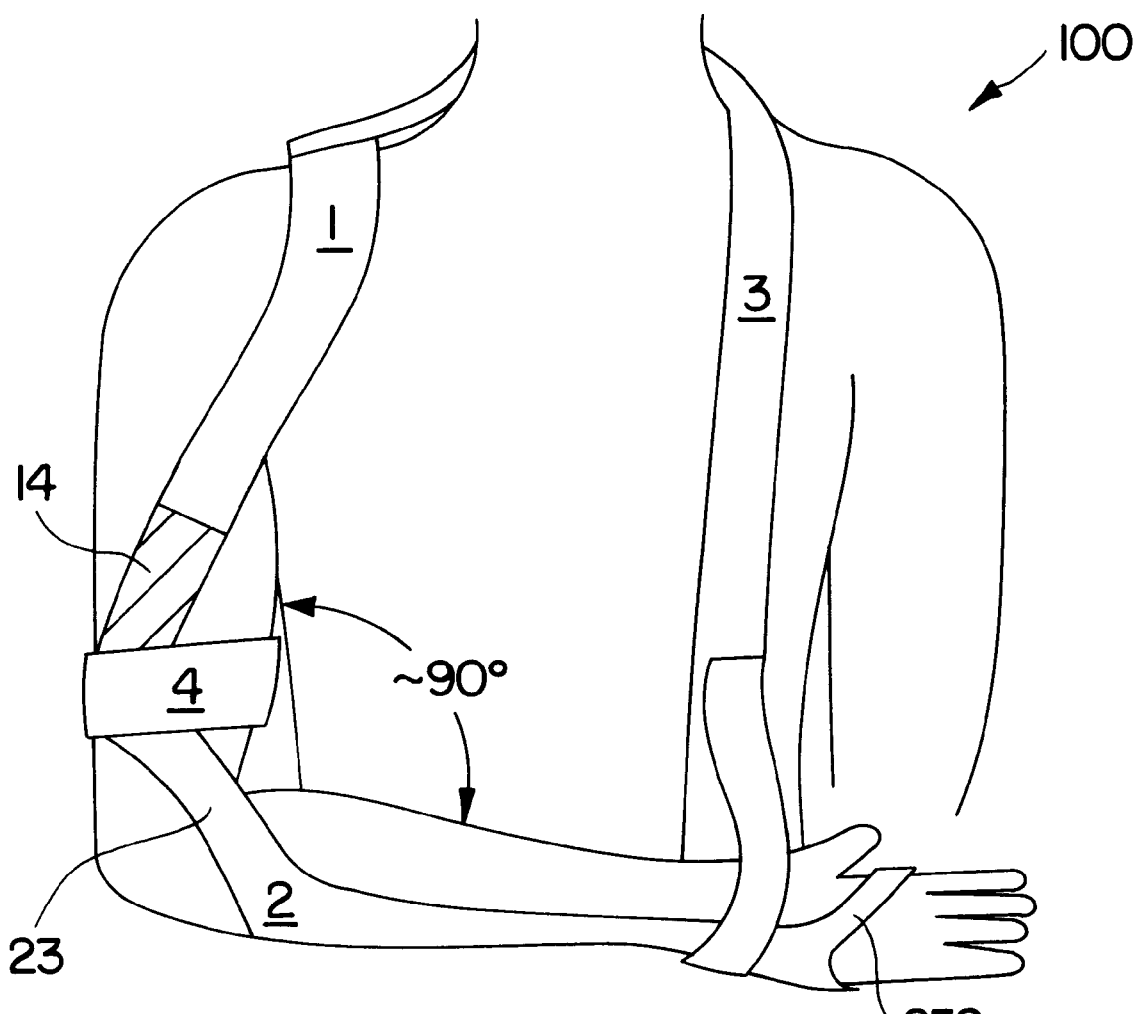
FIG. 3 shows the bandage according to the invention, comprising the upper-arm and forearm part together with connecting devices and straps, put on the right arm of the patient.

The bandage 100, which is shown in FIG. 3 and has been put on the right shoulder or the right forearm of the patient, is essentially composed of the upper-arm part 1 and the forearm part 2.

The upper-arm part 1 is fixed ventrally with respect to the forearm in the region of the wrist by means of a supporting strap 3 which runs from the shoulder to the region at the back of the neck. The supporting strap 3 is fixed by means of a touch-and-close fastener, so that a loop is formed around the forearm.

The forearm part 2 is fixed by means of a holding strap 4 which runs from the hand region dorsally in the lumbar region to the distal upper arm. The holding strap 4 is likewise fixed by means of a touch-and-close fastener.

The entire strap-guiding system, in a symbiosis, thus ensures the securing of the bandage position on the patient.

We claim:

1. A bandage (100) adapted for use on the shoulder and upper-arm region of a user, comprising an upper-arm part (1) and a forearm part (2), the upper-arm part (1) being of U-shaped design, and having a mouth (11), which lies in a region of the upper-arm part (1) in which a first limb (12) and a second limb (13) converge, is adapted to rest upon the shoulder during use, such that the first limb (12) is adapted to extend from the shoulder at the front of the user approximately as far as the elbow joint, and the second limb (13) is adapted to extend at the rear approximately as far as the elbow joint, each said first and second limbs having an elastic section situated at the ends thereof to ensure individual adaption to the anatomical shaping in the region of the shoulder and the upper arm of the elbow, to thereby securely guide the head of the upper arm, and the forearm part (2) having three sections (21), (22), (23), a central first section (21) which, when the forearm is bent in the front of the user at an angle of approximately 90°, is adapted to lie in the ulnar region of the forearm during use, a second section (22) which is connected to the second limb (13) of the upper-arm part (1) is adapted to extend at the rear over the elbow joint and merges into the first section (21) during use, a third section (23) which is connected to the first limb (12) of the upper-arm part is adapted to extend at the front over the elbow joint and merges into the first section (21) during use, the ends of the second section (22) and the third section (23) being connected to one another, a support strap (3) being attached to the upper-arm part (1), a holding strap (4) being attached to the forearm part (2), the holding strap (4) is adapted to extend from the hand region dorsally in the lumbar region to the distal upper arm and surrounds the latter laterally from the rear to the front, to thereby ensure that the forearm is securely fixed against the ventral area of the user, and a hand guide (25) comprising two restraints (251, 252) which adjoin the first section (21) of the forearm part (2), the two restraints (251,252) enclose an angle of 10° to 160° and are connected to one another by touch and close fasteners (253,254) at their distal ends, to thereby securely fix the hand.

2. The bandage according to claim 1, wherein the parts consist of a textile-lined foam or nonwoven.

3. The bandage according to claim 1, wherein the parts consist of a shaped foam or nonwoven.

4. The bandage according to claim 1, wherein an appropriately shaped reinforcement (16) is present in the upper-arm part (1), centrally in the region of the upper-arm part (1) where the mouth (11) is located.

5. The bandage according to claim 1, wherein reinforcements (24) are incorporated into the first section (21) of the forearm part.

6. The bandage according to claim 1, wherein the supporting strap (3) contains a partial cushion in a transition region positioned between the cervical vertebrae column and the shoulder girdle during use.

7. The bandage according to claim 1, wherein the straps (3, 4) consist of a laminated foam or a laminated nonwoven.

8. The bandage according to claim 1, wherein the straps (3, 4) have a good cushioning effect and under a load of approximately 50 N and have a preferred longitudinal extension of less than 35%.

\* \* \* \* \*

UNITED STATES PATENT AND TRADEMARK OFFICE
CERTIFICATE OF CORRECTION

PATENT NO.    : 6,099,489  
DATED         : August 8, 2000  
INVENTOR(S)   : Herzberg et al.

Page 1 of 1

It is certified that error appears in the above-identified patent and that said Letters Patent is hereby corrected as shown below:

<u>Title page,</u>
Item [54], delete "MEDICAL BANDAGE" and substitute -- ORTHOPEDIC ARM BANDAGE --

Signed and Sealed this

Twenty-sixth Day of February, 2002

*Attest:*

JAMES E. ROGAN
*Attesting Officer*     Director of the United States Patent and Trademark Office